United States Patent
Hart et al.

(10) Patent No.: US 7,252,805 B2
(45) Date of Patent: Aug. 7, 2007

(54) DEVICE FOR VAPORISING AND DIFFUSING OILS

(75) Inventors: Gerald Leslie Hart, deceased, late of Surbiton (GB); by Susan Hart, legal representative, Surbiton (GB); Colin William Brown, Bracknell (GB); Guy Edward Naish, Bicester (GB)

(73) Assignee: Givaudan SA, Vernier (CH)

( * ) Notice: Subject to any disclaimer, the term of this patent is extended or adjusted under 35 U.S.C. 154(b) by 346 days.

(21) Appl. No.: 10/928,912

(22) Filed: Aug. 27, 2004

(65) Prior Publication Data

US 2005/0175513 A1 Aug. 11, 2005

Related U.S. Application Data

(63) Continuation-in-part of application No. 10/483,546, filed on Jul. 14, 2004, now Pat. No. 7,014,819.

(30) Foreign Application Priority Data

Jul. 14, 2001 (EP) .................. 01117157

(51) Int. Cl.
*A61L 9/03* (2006.01)
(52) U.S. Cl. .............. 422/125; 392/395; 122/366
(58) Field of Classification Search ............. 122/366; 239/45, 51.5
See application file for complete search history.

(56) References Cited

U.S. PATENT DOCUMENTS

| 2,597,195 | A | * | 5/1952 | Smith ................. 422/125 |
| 4,346,059 | A | * | 8/1982 | Spector ............... 422/125 |
| 4,663,315 | A | | 5/1987 | Hasegawa et al. ........ 514/86 |
| 4,781,895 | A | | 11/1988 | Spector ............... 422/125 |
| 4,968,487 | A | | 11/1990 | Yamamoto et al. ....... 422/125 |
| 5,911,955 | A | | 6/1999 | Fullam ................ 422/125 |
| 6,144,801 | A | | 11/2000 | Leboux et al. .......... 392/390 |
| 7,014,819 | B2 | * | 3/2006 | Hart et al. ............. 422/125 |

FOREIGN PATENT DOCUMENTS

| DE | 3737272 A1 | 6/1988 |
| FR | 2 680 118 | 2/1993 |
| FR | 2 762 895 | 11/1998 |
| WO | WO 97/28830 | 8/1997 |
| WO | WO 99/22776 | 5/1999 |

* cited by examiner

*Primary Examiner*—E. Leigh McKane
(74) *Attorney, Agent, or Firm*—Norris McLaughlin & Marcus, PA

(57) ABSTRACT

A device which uses a heat source for heating and diffusing fragrant oils or insecticidal oils. The oil is contained in a reservoir remote from the heat source and the device comprises means for transferring the oil from a reservoir to a surface of a heat-absorbing means wherein heat from the heat source is transferred by conduction to said surface to volatilise the oil.

9 Claims, 4 Drawing Sheets

DEVICE FOR VAPORISING AND DIFFUSING OILS

This is a Continuation-in-Part of U.S. Ser. No. 10/483,546 filed Jul. 14, 2004 now U.S. Pat. No. 7,014,819.

This invention is concerned with devices that diffuse and vaporise oils, e.g. fragrant oils or insecticide oils, using heat source, e.g. a radiant heat source or a by conduction or convection.

Candles may be used as a heat source to diffuse fragrances. Typically a fragrant oil is incorporated in the body of a candle and the fragrant oil is released as the candle burns. However, the fragrant oils that may be used may be limited because they must not only be capable of being mixed in the candle matrix, they must also be capable of burning to ensure that the candle operates correctly.

Alternative devices are known that overcome the problems associated with fragrance-containing candles. The devices diffuse fragrant oils located in a reservoir external of a candle. Thus in U.S. Pat. No. 4,781,895 a fragrant oil contained in a porous cartridge, is contained in a reservoir supported directly above a candle which is burnt. The bottom of the reservoir is heated by the flame and thereby acts as a hot plate which heats the cartridge and volatilises the fragrant oil. However, application of a direct flame to an oil-containing cartridge may lead to overheating and combustion of the oil. Furthermore, as the cartridge contains a finite amount of oil which is not replenishable, the high initial concentration of oil will vaporise quickly to produce a burst of fragrance, but the release of oil will reduce quickly consistent with decreasing oil concentration in the cartridge. Still further, as the candle recedes so its heating effect on the reservoir will diminish and further exacerbate the uncontrolled vaporisation rate of the oil.

Another device is described in U.S. Pat. No. 5,911,955. This device again uses candle heat to volatilise a fragrant oil contained in a reservoir external of a candle. However, in this device the candle heat is not applied directly to the fragrant oil; rather the heat from the flame is conducted to the reservoir along radiation-absorbing fingers which extend outwardly from the candle flame and communicate with the reservoir. The reservoir is open to the atmosphere to permit egress of the vaporised oil. However, an open reservoir permits access to the oil by users and could also permit spillage of the oil, for example onto the flame. Further, as the heat from the candle must be transferred over a relatively large distance by conduction across the radiation-absorbing fingers, there will be a delay between lighting the candle and effective vaporisation. Still further, as the candle recedes, the heating effect of the flame on the fingers will diminish resulting once more in an uneven vaporisation rate of the oil.

It has now been found that it is possible to make a device that volatilises fragrant oils or insecticide oils and that is substantially free of disadvantages associated with the prior art devices.

The invention therefore provides in one of its aspects a device for vaporising and diffusing oils comprising a heat source and a reservoir containing fragrant oil and/or insecticide oil, the device comprising a wick having a first portion in communication with oil in the reservoir, and a second portion that abuts a first surface of a heat-absorbing body thereby to transfer oil to said first surface, wherein the heat-absorbing body is disposed between the wick and the heat source such that heat from the heat source is transferred by conduction to said first surface to volatilise the oil contained within the wick.

In particular, the invention provides a device for vaporising and diffusing oils, e.g. fragrant oils or insecticide oils comprising
  a container consisting of a wall having inside and outside surfaces, the inside surface defining a cavity to receive a heat source,
  a reservoir suitable for containing a fragrant oil or insecticide oil, and
  a porous rod that communicates with the reservoir and the outside surface of the container wall thereby to carry oil from the reservoir to the outside surface.

The device according to the invention has numerous advantages: It is relatively safe to use as heat is not applied to oil contained in the reservoir; heating of the oil is rapid when the device is actuated; and given that the heat source is always the same distance from the inside surface of the container, the oil is exposed to an essentially constant heat source resulting in substantially uniform vaporisation of the oil over a prolonged period of time. The container may take any shape or configuration although preferably it is cylindrical. It should be of suitable dimensions such that the cavity defined by the internal surface of the wall can receive a heat source such as a candle or a light bulb. One end of the container has a base to provide support for the heat source. The base may be formed integrally with the container wall, or it may be releasably fixed to the container using mechanical fixing means, e.g. container and base may be provided with co-operating threads.

The end of the container opposing the base may be closed, e.g. terminating in a ceiling portion which, like the base, may be integral with, or releasably fixed to, the wall of the container. Alternatively, the opposing end may be open, that is, the inner surface of the container wall defines an aperture. When the container is formed with such an aperture, advantageously the container tapers in the direction of the aperture such that if the device were to topple over the heat source, e.g. a candle, could not exit the device through the aperture, even in the case where the aperture is large enough to allow insertion of the candle.

The container wall may be provided with one or more apertures towards its bottom and towards its top to permit ingress and egress of air. This feature will allow air to flow through the container which is important to ensure good burning and convection in the event that the radiant heat source is a candle.

A variety of materials may be used in the construction of the container provided they are non-flammable, capable of conducting heat from the heat source from the inside surface of the wall to the outside surface, impervious and stable to fragrant and insecticide oils, and possess sufficient mechanical strength to support the container's weight and the weight of the porous rod. Suitable materials include metals such as aluminium, steel and copper, glass and ceramics, and even certain plastics materials that are heat resistant, for example certain fire resistant polyacrylates. The thickness of the container wall must be such to impart the requisite mechanical strength and also to permit rapid heat transfer from the inside surface to the outside surface of the wall. For reasons of allowing light from a heat source to radiate from the device to enhance the aesthetics of the device, the container may be provided with appropriately arranged apertures or certain portions or even all of the container may be formed of transparent materials.

The reservoir is preferably in the form of a closed receptacle. This is in contrast to the device described in U.S. Pat. No. 5,911,955 wherein the reservoir is open in order that the heated oil contained therein may volatilise and escape the device by diffusion into the surrounding atmosphere. In the present invention, the oil is not volatilised in the reservoir and so the reservoir may be closed to prevent access to the oil by a user and also to prevent spillages if the device is toppled over.

The reservoir may be of any shape or configuration and may be made of any material provided that it is impervious and stable when containing fragrant or insecticidal oils, and possesses sufficient mechanical strength. It, or a part thereof, may be made of transparent material which has the advantage of providing the user with a visual cue when the level of oil is too low and needs replenishing. It may be formed integrally with the container. However, in a preferred embodiment the reservoir is formed separately from the container and the two may be connected prior to use by any suitable fixing means, e.g. releasably fixed, for example by mechanical fixing means, e.g. co-operating threads or a bayonet fitting. In a most preferred embodiment, the reservoir forms a base supporting the container.

An opening is provided in the reservoir in order to permit access of the porous rod to the oil contained in the reservoir. The opening is preferably dimensioned such that it tightly embraces the porous rod to form a tight seal thereby preventing uncontrolled evaporation of the oil, or spillage in the event that the reservoir is toppled over. Additionally, the tight seal may promote good capillary action of the oil exiting the reservoir along the porous rod.

Depending on the nature of the porous rod, it may be difficult to achieve a desirably tight seal. Further, if the opening to receive the porous rod and the opening to permit refilling of the reservoir are the same, it may be difficult to re-insert a porous rod made, for example of certain soft or pliable materials used in the manufacture of wicks. Accordingly, the reservoir in a preferred embodiment may be equipped with a sealing member that assists insertion and removal of the porous rod from therefrom, that consists of a hollow shaft portion, defining a receiving passage to tightly receive and embrace a portion of the porous rod, and a collar portion at one end of the shaft which is adapted to fit over the opening in the reservoir in sealing relationship therewith. When the sealing member is placed over the opening in the reservoir, the collar fits tightly over the opening to seal the reservoir and the hollow shaft containing the porous rod projects into the reservoir. The end of the shaft remote from the collar is provided with an aperture such that the tip of the porous rod projects outwards of the aperture and into the oil. The sealing member may be made of any suitable material, e.g. plastics material or metal, and may be of the same material as the reservoir and is preferably formed as a one piece unit for ease and low cost of manufacture.

The opening in the reservoir for receiving the porous rod does not have act as an opening for refilling the reservoir, for example the reservoir may be a use-once device disposable after use and as such a refilling operation is not appropriate or necessary. Alternatively, the reservoir and container may be integrally formed such that the porous rod (and the opening in the reservoir therefore) may not be readily accessible to the user. In such an embodiment there may be an additional opening in the reservoir for the refilling operations, and these additional openings may be provided with releasable closure means.

A reservoir which is detachable from the container as hereinabove described forms an independent aspect of the present invention. It may be provided, for example in the form of a pre-filled container that may be made of a material that can be readily discarded after the oil is extinguished.

The opening in the reservoir for receiving the porous rod may be sealed during storage, for example by means of a screw cap or by a foil cap.

Oil transfer from the reservoir to the outer surface of the container wall is effected by means of the porous rod. The porous rod may be of one-piece construction which passes from the reservoir through an opening provided therein and thereafter along the outer surface of the container wall.

In an alternative embodiment, however, the porous rod may be formed of more than one piece, e.g. two pieces. A first piece consists of a portion of elongate porous rod that projects into the oil-containing reservoir in one direction terminating in a tip, and terminates at its other end in the form of a first porous pad, which fits over the opening in the reservoir in sealing relationship. Alternatively, when a sealing member is employed as hereinabove described, the first porous pad, rather than itself being in sealing relationship with the opening in the reservoir, is supported on the collar portion of the sealing member which provides the sealing relationship with the opening in the reservoir.

A second piece of the porous rod consists of a second porous pad which is located on the outer surface of the container wall and conforms substantially with the first porous pad such that when reservoir and container are connected, first and second porous pads engage each other to allow oil to flow, e.g. by capillary action, from the reservoir to the first porous pad and there to the second porous pad. Extending from the second porous pad and comprising part of the second piece of the porous rod is a portion of the porous rod that is fixed to the outer surface of the container wall which receives heat from the heat source.

The portion of the porous rod which is fixed to the outer surface of the container wall may, in its simplest form, consist of a single rod extending in one direction along the outer surface of the container wall. However, in order to increase the surface area of porous rod in contact with the container wall, it may describe a convoluted pathway across the outside surface of the container wall, or there may be a plurality of porous rods or strips extending outwards of the second porous pad and across the container wall. Other ways of increasing the surface area of the rod fixed to the outer surface of the wall will be apparent to the skilled person. The porous rod may describe a decorative path across the container wall to increase eye appeal of the device. However, irrespective of the path described by the porous rod, it is important that it is fixed in intimate contact with the container such that efficient heating of the rod and oil contained therein may be effected.

The portion of the porous rod that extends into the reservoir may be substantially surrounded by a barrier material which is impervious to the oil and therefore prevents contact and therefore uptake of oil by the porous rod. The barrier material permits exposure of the oil only to a relatively small tip portion of the porous rod. This has the advantage that if the reservoir topples over, the tip portion lifts clear of the oil and thereby oil transfer to the container wall is discontinued to prevent possible leakage until such time as the device is restored to its correct position. It is apparent that in one embodiment of the invention the aforementioned "barrier material" may be provided by the hollow shaft portion of the sealing member referred to hereinabove.

The porous rod may be formed of any natural or synthetic material and one skilled in the art may select materials to obtain the desired oil transfer properties without any inventive thought and without undue burden, for example the rod may be formed of natural or synthetic, woven or unwoven material typically used in wicks. It may take any suitable shape and is not limited to being generally circular in cross-section, for example it may have the shape of a flattened strip.

In its simplest form therefore, the device consists essentially of a container, a reservoir and a porous rod communicating with the reservoir and the container. Whereas this device solves the problem of spillage of the oil from the reservoir, in particular spillage onto the radiant heat source, and may permit of rapid and uniform vaporisation of the oil, nevertheless the user may still come into contact with relatively small amounts of oil if he or she brushes against an exposed portion of the porous rod. For this reason, in a preferred embodiment of the invention the device is provided with a shroud which substantially surrounds at least that part of the container that carries the porous rod or strip.

The shroud serves to prevent users from touching the oil-impregnated porous rod and also prevents the user from inadvertently touching the container which may be rather hot when in use. It may be of any shape or configuration consistent with this purpose. However, it may take a decorative shape, for example the petals on a flower for aesthetic reasons. It should not completely enclose the container in order to ensure that volatilised oils may diffuse out of the device. Alternatively, the shape may be essentially practical, or even safety-oriented. For example, the shroud may be triangular in transverse cross-section and the rod from which evaporation takes place may be positioned opposite to the side of the triangle. This ensures that, if the device is accidentally tipped over and the candle remains alight, the rod is never directly above candle flame, even if there is one rod per side, as is possible.

The shroud may be of separate construction with respect to the other components of the device. If formed of separate construction it may be free standing with respect to the other components of the device or it may be fixed to the container and/or the reservoir, for example releasably fixed to the container and/or reservoir, e.g. with mechanical fixing means.

The heat source may be provide by a lighted candle or a light bulb or any other suitable means, for example using focused rays of the sun, and the base of the container may be adapted accordingly to support the heat source, for example the base may comprise candle holding means, or may comprise a socket for receiving a light bulb.

The heat source may be introduced into the container by means obvious to those skilled in the art. Thus, for example the heat source, e.g. candle may be place into position in the container by means of an aperture provided in the container for that purpose. The shroud may be removed for this purpose or it may be provided with an aperture co-operating with the aperture in the container for this purpose. Other methods of placement and removal of the heat source, however, are not precluded as will be obvious to the person skilled in the art.

Once actuated, the heat source heats the inner surface of the container wall. Due to the nature of the container material and/or given that it is very thin, the heat traverses the wall and heats the oil more quickly than in prior art devices. As the porous rod is heated so the oil contained therein heats up, volatilises and diffuses out of the device. The evaporation of the heated oil in turn drives more oil out of the reservoir and into the rod adjacent to the heated outer surface of the container wall.

When the oil or the heat source is exhausted, it is a simple matter to replace the heat source or refill or replace the reservoir.

In a further, especially preferred embodiment of the invention, the porous rod from the reservoir to the heated surface is a wick, which has the form of a hollow cylinder (the "wick cylinder") having curved inner and outer surfaces, and with a lower closed end. From this closed end, a solid rod depends in a direction away from the wick cylinder and coaxially with it. This rod goes into liquid in the reservoir and draws liquid into the wick cylinder. Within the wick cylinder nests in heat-conducting contact therewith a container in the sense previously described, having inside and outside walls and a cavity adapted to receive a heat source, preferably a candle. The container, which is made from any suitable material that is able to transmit heat by conduction without being damaged by it, such as metal, glass, plastics or ceramic, acts as a heat conductor for the heat from the candle to the wick cylinder. This causes liquid to evaporate from the wick cylinder into the atmosphere.

In a preferred embodiment, the wick cylinder is encased in a cap, preferably an extension of a closure of the reservoir. This cap has an annular transverse cross-section and encases the wick cylinder on both sides, except for orifices as hereinafter described. The cap has a central re-entrant portion that matches the shape of the wick cylinder, and that is dimensioned such that the container nests within the cap and is in heat-conducting contact therewith. This cap has at least one orifice on the outer side thereof, remote from the candle, through which volatilised liquid can escape from the wick cylinder. In a variant of this, the cap is equipped with an upper cap, which is rotatable about the cap. This upper cap bears a number of orifices equal to that of the cap, the two sets of orifices being sized and placed so that rotation of the upper cap can partially or completely block the orifices of the cap and hinder or prevent vaporised liquid from escaping.

In a preferred version of this embodiment, a flange extends circumferentially from the container from a point above the end of the wick cylinder, to such an extent that the wick is protected from material falling from above. Practically, this means that it extends beyond the diameter of the wick cylinder, or, when a cap or an upper cap is used, beyond the diameter of the cap or upper cap. This flange is generally planar and circular, but may be made in any desired shape or dimension. It gives an added safety factor in that, if the candle is lit by means, say, of a match and the match is dropped, there is no possibility of the match contacting the wick cylinder and igniting any flammable material therein. The flange may extend from the upper circumferential lip of the container, or, in the case of the container extending substantially beyond the rod cylinder, from some point intermediate between the top of the wick cylinder and the upper lip of the container, in the form of a vane. The flange is preferably perforated, to permit vaporising liquid from the wick cylinder that is emerging from an orifice or orifices below the flange, to pass through.

In this embodiment, the porous rod or wick may be formed in two parts, the rod that makes contact with the liquid and the cylinder with the closed lower end provided with an aperture to receive the rod. Alternatively, the cylinder may be made in a cup shape and the rod extending downwards into the liquid may be equipped with a porous flat plate, on which plate the cup sits, and liquid passes from the flat plate into the porous cup. A further possibility is that the wick may be made in a single piece.

The device according to the present invention is useful to diffuse oils, e.g. fragrant oils or insecticide oils, into surroundings in need thereof. Any of the oils known in the art that find use in vaporising and diffusing devices may be used in the device of the present invention. In addition to the use of neat oils, the device may also be employed to vaporise and diffuse oils in suitable solvents, for example oils in water or in ethanol.

The invention is now further described with reference to the drawings. These drawings depict preferred embodiments and do not limit the invention in any way.

Figure 1:
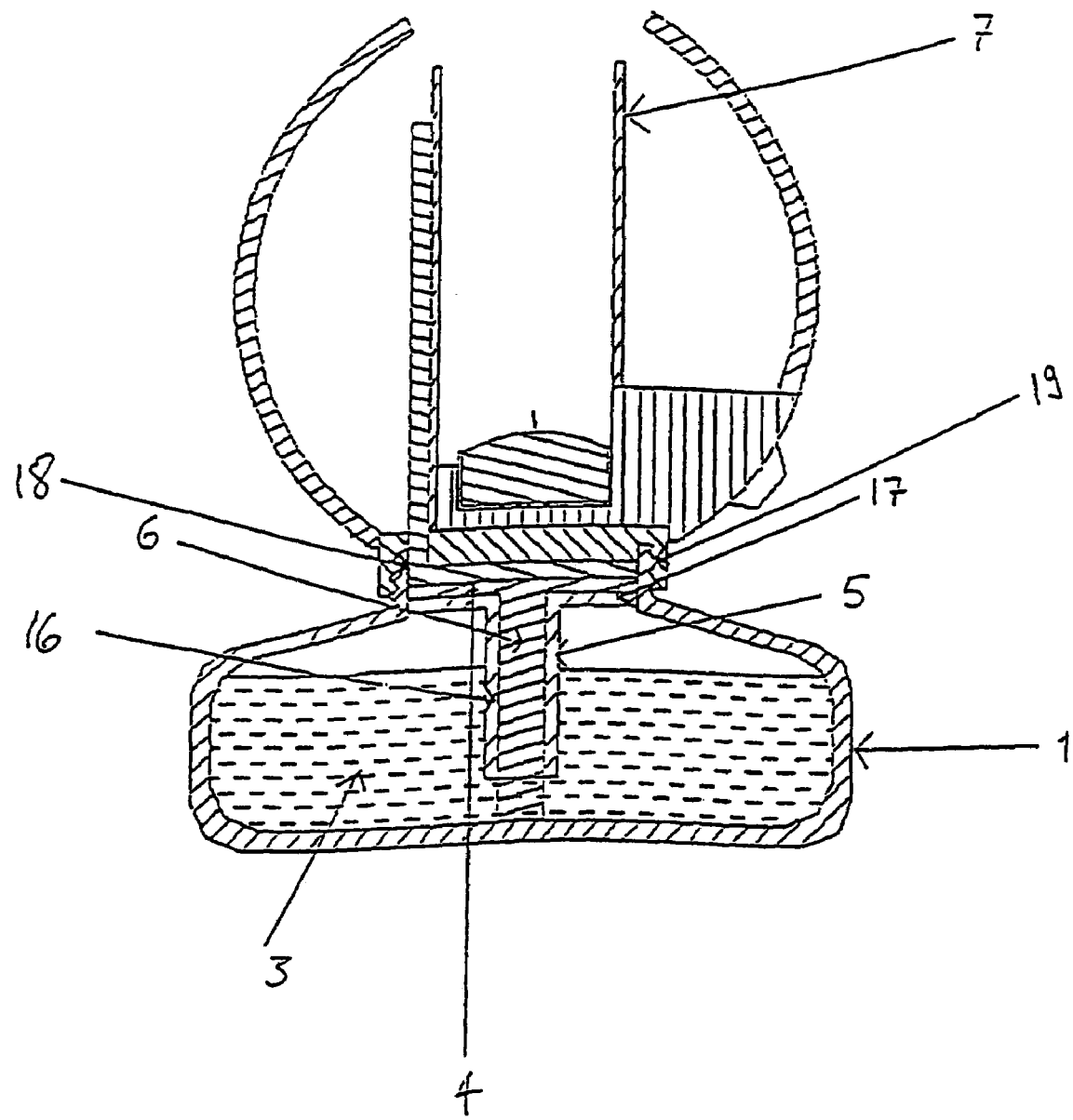
FIG. 1 depicts a view of the device in cross section with candle-holder inserted.

The device shown in FIG. 1 is in the form of a lantern and consists of a reservoir (1), in the form of a broad base to impart stability to the device, containing oil (3). The reservoir is sealed to prevent spillage, with a sealing member (5). The sealing member is essentially T-shaped in cross section and consists of a hollow shaft (16) containing a portion of a porous rod or strip (6) which extends downwardly into the oil (3), and an integrally formed collar portion (17). Seated on top of the collar portion (17) is a porous pad (4) which is in contact, and may be integral, with the porous rod or strip (6). The reservoir (1) has a neck portion (18) equipped with a thread (19) on its outer surface.

Figure 2:
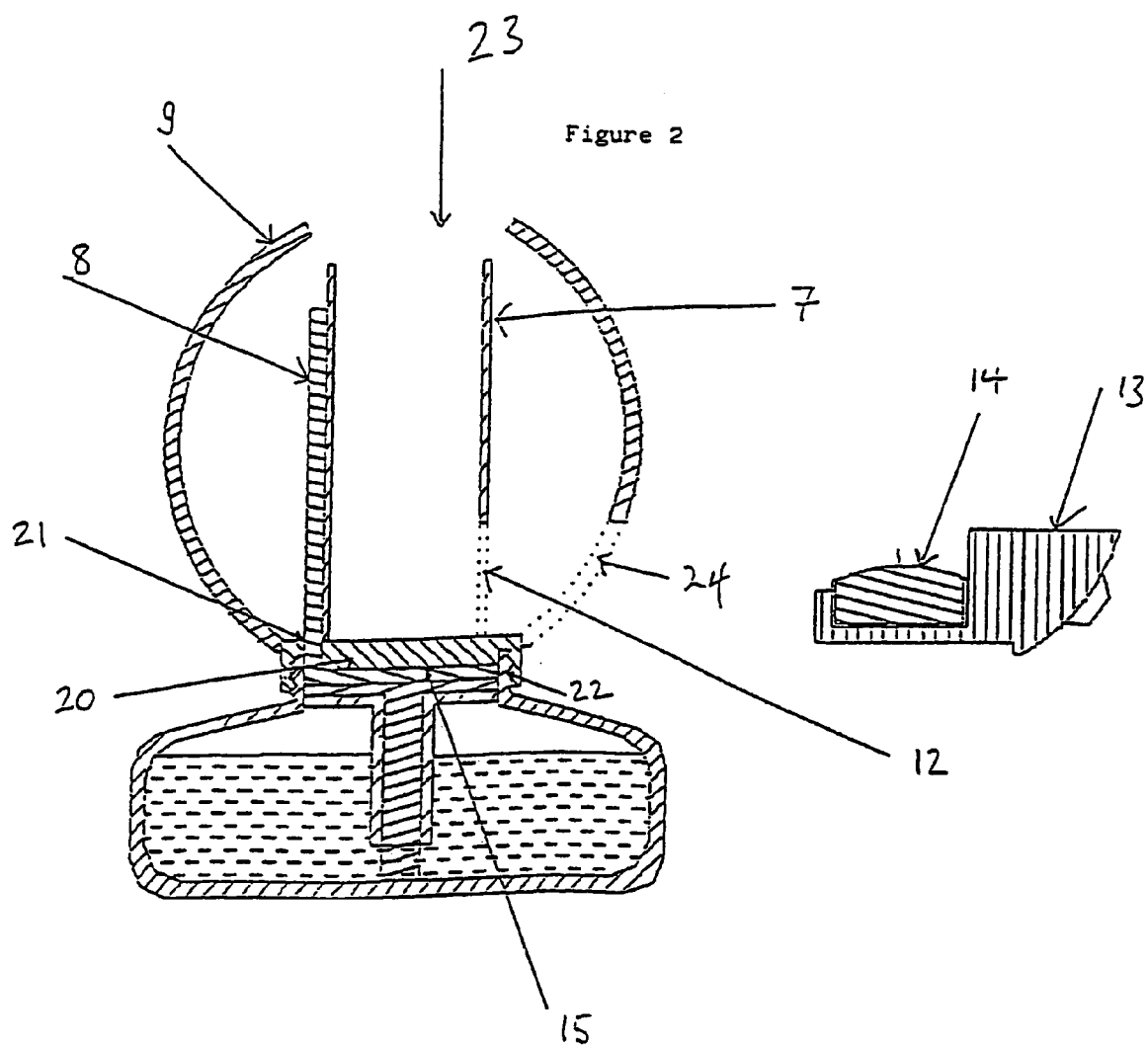
FIG. 2 depicts the device in cross section with the candle holder removed

Referring to FIG. 2, the container consists of a generally cylindrical open-topped funnel (7). Towards its bottom, the funnel (7) is provided with an aperture (12) adapted to receive the heat source, e.g. a candle (14). The candle is situated in a candle holder (13) and the candle holder may be slid laterally in and out of the aperture (12) when the candle needs to be removed and replaced. On the outer surface of the funnel (7) there is fixed a porous rod (8) which contains oil drawn from the reservoir, for example by capillary action. The bottom of the funnel is provided with a base (20) which supports the candle holder (13) when it is inserted in the device. The base is provided with a small aperture (21) through which the porous rod (8) extends to a position below the base where it contacts, and may be integral with, a porous pad (15) (in the embodiment shown 8,15 are integral). The container is equipped with a thread (22) below the base (20) which is adapted to co-operate with the thread (19) on the neck portion of the reservoir (1) to releasably connect container and reservoir.

Surrounding the funnel (7) is a shroud (9) which is formed integrally with the funnel (7). The shroud has an aperture (23) to permit egress of volatilised oil. The shroud is also provided with an aperture (24) which is in general alignment with the aperture (12) in the funnel (7) to permit insertion and removal of the candle holder (13).

In use, the reservoir (1) is fixed to the funnel (7) by the co-operating threads (19,22) such that the porous pads (4) and (15) come into contact. Oil then rises through capillary action via (6), (4) and (15) to the porous rod (8). The lighted candle (14) and its holder (13) are inserted into the funnel via the apertures (12, 24). Radiant heat from the candle heats the wall of the funnel (7) which, in turn, heats and volatilises the oil in the rod (8). The oil vapours then pass up the space between the container and the shroud and out of the aperture (23). The act of vaporisation of oil from the porous rod (8) acts to draw further oil from the reservoir via (6, 4, 15) to the porous rod where it, in turn, is vaporised.

When the oil in the reservoir is exhausted, the reservoir and funnel are disconnected; the sealing member (5) is removed and either fresh oil is poured into the reservoir or the reservoir is discarded and a new reservoir filled with oil is provided. The device may be reconnected carrying out these operations in reverse. Similarly, once the candle is exhausted it is removed with its holder through the apertures in the funnel and shroud; a fresh candle is inserted into the holder and is lit before the holder and freshly lit candle are placed into the funnel.

Figure 3:
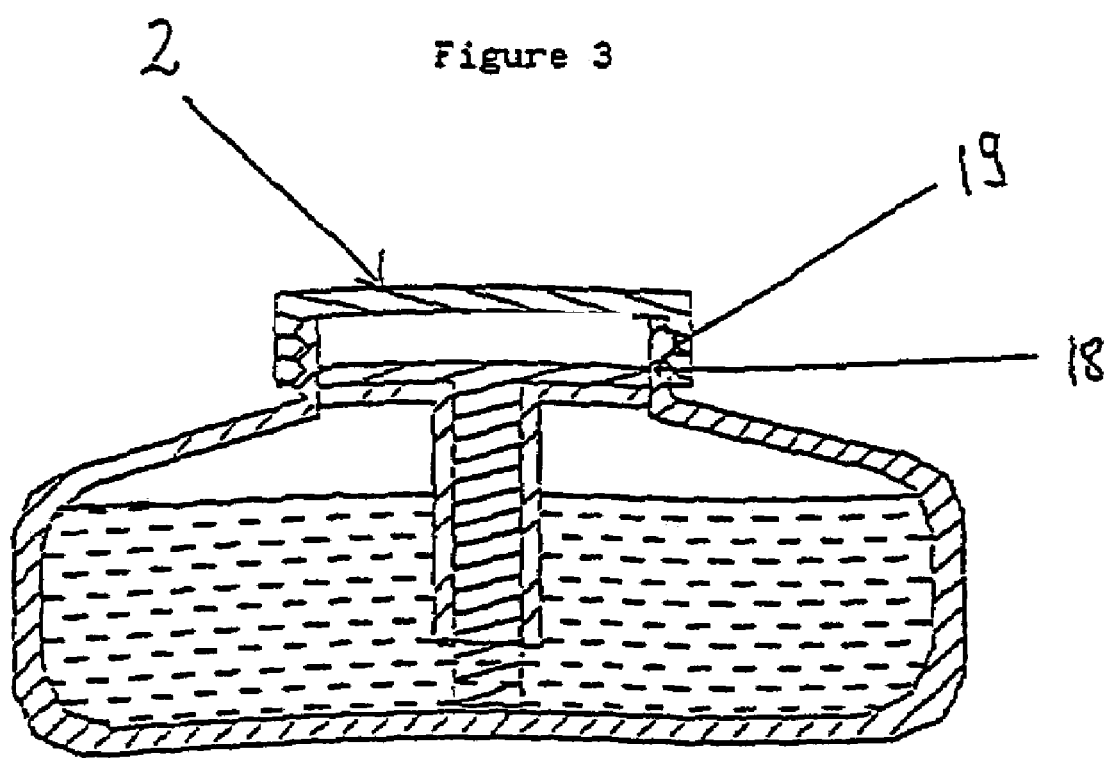
FIG. 3 depicts the reservoir in cross section disconnected from the remainder of the device.

When disconnected from the device (see FIG. 3) the reservoir may be closed with a cap (2) that may be equipped with a thread adapted to co-operate with the thread (19) on the outer surface of the neck portion (18). Closure of the reservoir need not however, be achieved using a threaded cap, for example closure may be achieved using a removable foil sheet.

Figure 4:
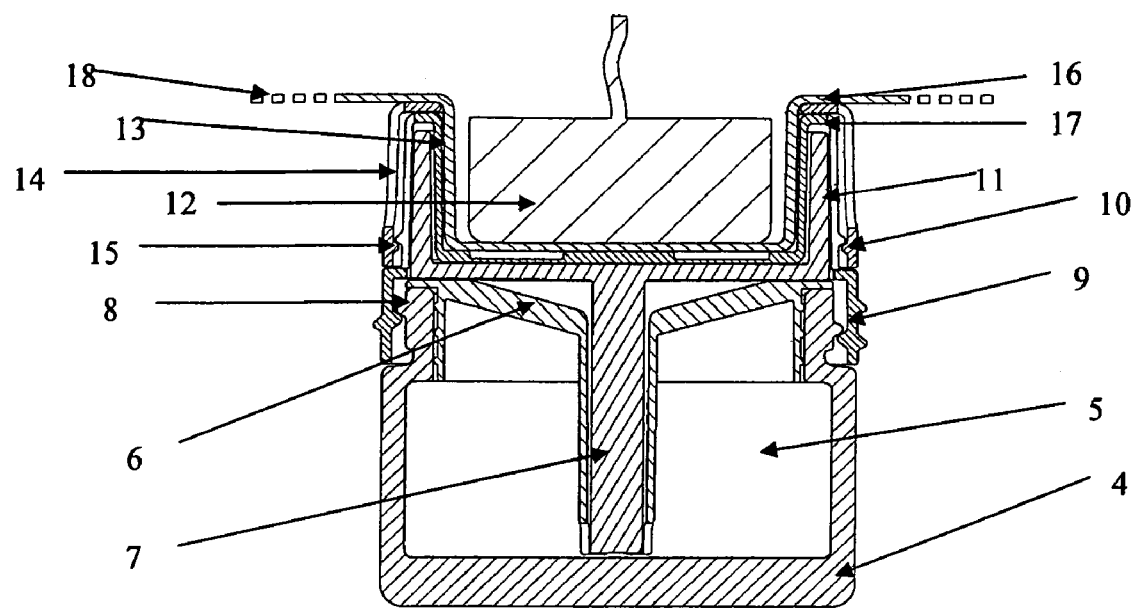
FIG. 4 depicts a longitudinal cross-section of a further preferred embodiment of the invention.

Referring now to FIG. 4, a reservoir 4 containing a volatile liquid 5 is equipped with a porous wick 7, having the shape of a hollow cylinder closed at the bottom end, with a cylindrical solid rod projecting coaxially with and downwardly from the closed bottom end. This wick is held in position by a wick support 6, which has the form of a funnel, the downwardly-projecting "nozzle" of the funnel being dimensioned so as to accommodate the solid cylindrical rod portion of the wick 7 and therefore support the wick.

The reservoir 4 has a neck 8 to which a cap is attached by cooperating screw threads. The cap has two parts, an upper cap 9 and a lower cap 10. The lower cap bears at its lower end the abovementioned screw threads. The upper part of this cap has a cylindrical-shaped re-entrant portion 11 with a flat bottom, adapted to receive a candle container 13, which holds a candle 12. The walls of the cap surrounding the re-entrant portion are hollow (in transverse cross-section they have the form of an annulus) and are adapted to accommodate the circular wall of the cylindrical wick 7. The face of the cap wall remote from the candle 12 has apertures 14 adapted to release evaporating liquid from the cylindrical portion of the wick 7 within the cap.

The upper cap is fitted to the lower cap by snap fitting by means of cooperating circumferential projections 15 on the outer wall of the lower cap and the inner wall of the upper cap. The upper cap is basically a cylinder with a turned-over top 16, which top rests on top of the hollow wall of the lower cap. The relative dimensions of the upper and lower caps are such that the upper cap can be rotated around the lower cap. The upper cap is also provided with a series of apertures 17 placed circumferentially around it, and arranged with respect to the apertures 14 of the lower cap so that the access to the atmosphere of the vapour from the wick can be partially or completely closed off by turning the upper cap.

The candle container 13 has the form of a hollow metal cylinder, open at the upper end, the lower closed end supporting a candle 12. At the upper open end of the container, there is a planar, circumferential, perforated flange 18 formed as a continuation of the upper end of the container, this flange resting on the turned-over top 16 of the upper cap 9.

In operation, the candle 12 is lit and the resulting heat is conducted through the container 13 and the hollow walls of the lower cap 9 to the cylindrical part of the wick 7, thus causing evaporation of liquid from the wick to the atmosphere via the apertures 14 and 17.

The flame of the candle is completely isolated from the liquid and the flange protects the wick from any contact with any ignited material inadvertently falling from above.

Figure 5:
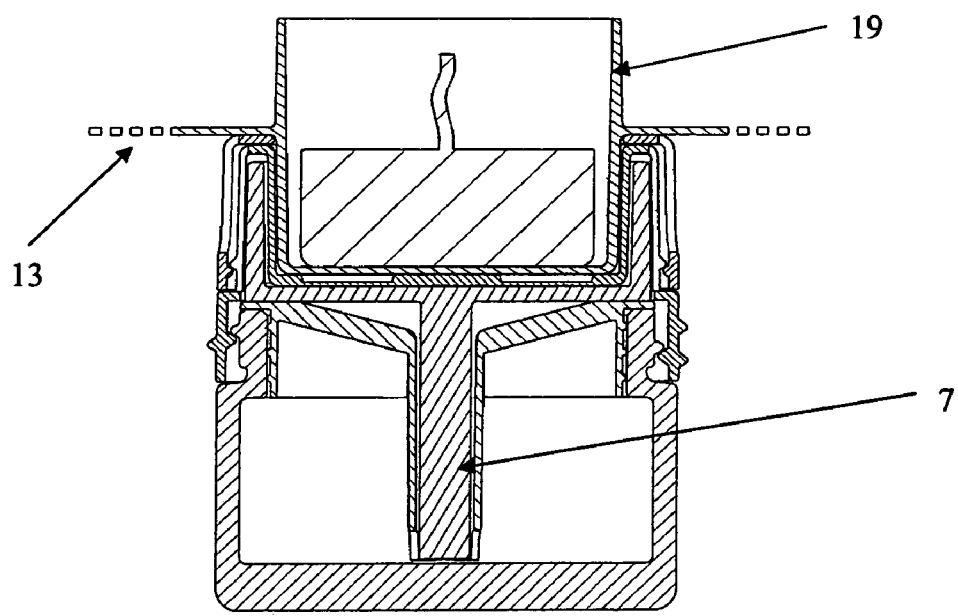
FIG. 5 depicts a longitudinal cross-section of a variation of the embodiment of FIG. 4.

FIG. 5 depicts a modification of the apparatus of FIG. 4. In this case, the container 13 is equipped with a cylindrical extension 19 extending upwardly from the candle. In this case, the flange remains in the same place with respect to the lower cap 9, but the cylindrical part of the container now extends above it. This increases the surface area available for heating and allows better evaporation.

The invention claimed is:

1. A device for vaporising and diffusing oils comprising:
a container made of heat-conducting material and consisting of a wall having inside and outside surfaces, the inside surface defining a cavity to receive a radiant heat source,
a reservoir suitable for containing a fragrant oil or insecticide oil, and
a porous rod that communicates with the reservoir and the outside surface of the container wall thereby to carry oil from the reservoir to the outside surface, the porous rod being a wick that has a portion that has the form of a cylinder having inner and outer curved sides and being closed at one end, from which closed end depends coaxially with and away from the cylinder, a solid cylindrical rod adapted to contact the oil; and
at least part of the container has the form of a cylinder that is adapted to hold a heat source and that is configured so as to be nestable within the wick cylinder and in heat-conducting contact therewith.

2. A device according to claim 1, wherein tile curved surface of the wick cylinder is completely surrounded on both inner and outer sides by a cap having a re-entrant portion into which fits the container in heat-conducting contact, the cap having at least one orifice on a surface remote from the container, to permit the vaporisation of liquid into the atmosphere.

3. A device according to claim 1, wherein the container comprises a flange extending outwardly circumferentially therefrom, to such an extent that the rod is protected from contact with material falling vertically from above.

4. A device according to claim 1 wherein the container is surrounded by a shroud which prevents the porous rod being contacted by a user.

5. A device according to claim 1 wherein the heat source is a candle or a light bulb.

6. A device according to claim 5 wherein the reservoir and the container are detachable.

7. A device according to claim 5, wherein the heat source is a candle and the container is constructed such that the candle is at least partially visible through it.

8. A device according to claim 1 in the form of a lantern comprising a container, a reservoir serving as a base for the container, and a shroud surrounding the container.

9. A device according to claim 1 wherein the said oils are fragrant oils or insecticide oils.

* * * * *